United States Patent
Shi

[19]

[11] Patent Number: 6,083,634

[45] Date of Patent: * Jul. 4, 2000

[54] ORGANOMETALLIC COMPLEXES FOR USE IN LIGHT EMITTING DEVICES

[75] Inventor: Song Q. Shi, Phoenix, Ariz.

[73] Assignee: Motorola, Inc., Schaumburg, Ill.

[ * ] Notice: This patent is subject to a terminal disclaimer.

[21] Appl. No.: 08/886,553

[22] Filed: Aug. 11, 1997

Related U.S. Application Data

[63] Continuation-in-part of application No. 08/304,451, Sep. 12, 1994.

[51] Int. Cl.[7] .................................................. H05B 33/14
[52] U.S. Cl. ................ 428/690; 428/691; 428/704; 428/917; 427/66; 313/504; 313/506
[58] Field of Search .................................. 428/690, 691, 428/704, 917; 427/66; 313/504, 506

[56] References Cited

U.S. PATENT DOCUMENTS

| | | | |
|---|---|---|---|
| 5,382,452 | 1/1995 | Bruno et al. | 427/215 |
| 5,432,014 | 7/1995 | Sano et al. | 428/690 |
| 5,817,431 | 10/1998 | Shi et al. | 428/690 |

FOREIGN PATENT DOCUMENTS

| | | |
|---|---|---|
| 0579151 | 1/1994 | European Pat. Off. . |
| 0726304 | 2/1995 | European Pat. Off. . |
| 0652273 | 5/1995 | European Pat. Off. . |
| 2037284 | 7/1980 | United Kingdom . |

OTHER PUBLICATIONS

"Castor Oil to Chlorosulfuric Acid," Encyclopedia of Chemical Technology, Third Edition, vol. 5, John Wiley & Sons, pp.351–353, 1979.

"Complex Compounds of Metals with Some Nitrogen–Containing Ligands XXXIII. Spectral Properties of Complexes of Bivalent Metals with 2–(o–Hydroxphenyl) benzoxazole", L.I. Kuznetsova et al., pp. 1–11, Mar. 1976.

Chemical Abstracts, vol. 119, No. 26, Dec. 27, 1993, abstract No. 285033, Hoveyda et al. "Coordination Chemistry of 2–(2'–Hydroxyphenyl)–2–Benzoxazole eith Gallium(III)and Aluminum(III): Two Uncommon Group 13 Metal Enviroments Stablizied by a Biologically Relevant Binding Group", XP002090752.

Chemical Abstracts, vol. 97, No. 8, Aug. 23, 1982, abstract No. 65428, Das et al., "Complexes of 2–(o–Hydroxyphenyl) Benzothiazoline with Some Bivalent Metal Ions" XP002090753.

Chemical Abstracts, vol. 84, No. 8, Feb. 23, 1976, abstract No. 51722, Lorenz et al. "Copper(II) and Zinc(II) Complexes of 2–(o–Hydroxyphenyl) Benzoxazole and–Benzothiazole" XP002090754.

"A Novel Blue Light Emitting Material Prepared from 2–(o–Hydroxphenyl)Benzoxazole", Nakamura et al., Chemistry Letters, (1994), pp. 1741–1742.

*Primary Examiner*—Marie Yamnitzky
*Attorney, Agent, or Firm*—Eugene A. Parsoms; William E. Koch

[57] ABSTRACT

A new class of organometallic complexes for use in electroluminescent (EL) devices and a method of preparation are disclosed. The organometallic complexes are prepared by mixing organic ligands with metal salts and a layer is formed in an EL device by vacuum evaporation. The organometallic material in the EL device forms a light emission layer.

35 Claims, 2 Drawing Sheets

ORGANOMETALLIC COMPLEXES FOR USE IN LIGHT EMITTING DEVICES

CROSS REFERENCE TO RELATED APPLICATION

This is a continuation-in-part of copending, commonly-assigned U.S. patent application Ser. No. 08/304,451, filed Sep. 12, 1994.

STATEMENT REGARDING FEDERALLY SPONSORED RESEARCH OR DEVELOPMENT

The U.S. Government has rights in this invention, pursuant to Cooperative Research and Development Agreement No. SC93/01171 between Sandia Corporation and Motorola, Inc.

FIELD OF THE INVENTION

This invention relates to organic electroluminescent materials used in devices such as light emitting diodes.

BACKGROUND OF THE INVENTION

Organic electroluminescent (EL) devices, consisting of thin layers of organic molecules sandwiched between transparent and metallic electrodes, are ideal candidates for use in display applications since they are inexpensive to fabricate and capable of a full range of colors.

In the prior art, a class of organic EL devices that have exhibited high efficiency and good stability, are those based on metal complexes of 8-hydroxyquinoline and its derivatives (Vanslyke et al. U.S. Pat. No. 4,539,507; 5,150,006). The emission of colors ranging from blue to red has been achieved by different dye doping of the metal complexes. However, light emitting devices (LED) based on the prior art dye doped metal complexes have limited current carrying capability, which curtails the brightness of the resulting devices. This is especially true when the prior art dye doped metal complexes are used in light emitting devices (LED) designed to emit in the blue range. For example, a prior art LED with an emission maximum at 470 nm produced approximately 1300 cd/m$^2$ at 15 volts of operating voltage.

It is a purpose of this invention to provide a class of new organometallic complexes for use in light emitting devices.

It is another purpose of this invention to provide preparation methods for the disclosed organometallic complexes for use in light emitting devices.

It is still another purpose of this invention to fabricate light emitting devices with the disclosed organometallic complexes.

It is yet another purpose of the present invention to provide light emitting devices with high brightness.

It is a further purpose of the present invention to provide light emitting devices for emission in the blue range with improved efficiency.

SUMMARY OF THE INVENTION

The above problems and others are at least partially solved and the above purposes and others are realized in a new class of organometallic complexes having one of the general formulas

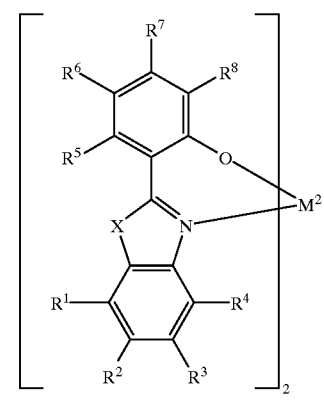

and

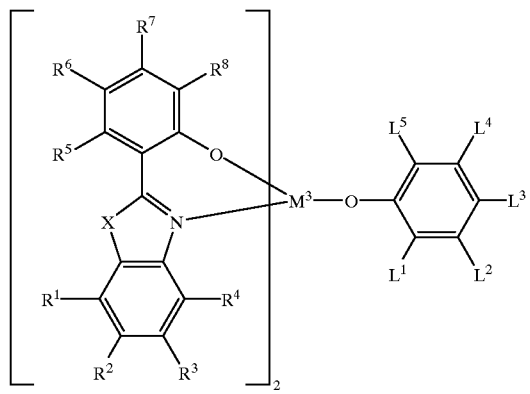

where:
M$^2$ is a divalent metal;
M$^3$ is a trivalent metal;
X represents one of O, S, NH and CH$_2$;
R1 to R8 represent substitution possibilities at each position and each represent hydrogen or hydrocarbon groups or functional groups; and
L1 to L5 represent substitution possibilities at each position and each represent hydrogen or hydrocarbon groups or functional groups.

In addition, the preparation of the new class of organometallic complexes is novel and the complexes are utilized to form new and novel organic electroluminescent devices.

DESCRIPTION OF THE PREFERRED EMBODIMENTS

The present invention is directed to a class of new organometallic complexes for use in organic light emitting devices which, in general, consist of thin layers of organic molecules sandwiched between transparent and metallic electrodes.

Figure 1:
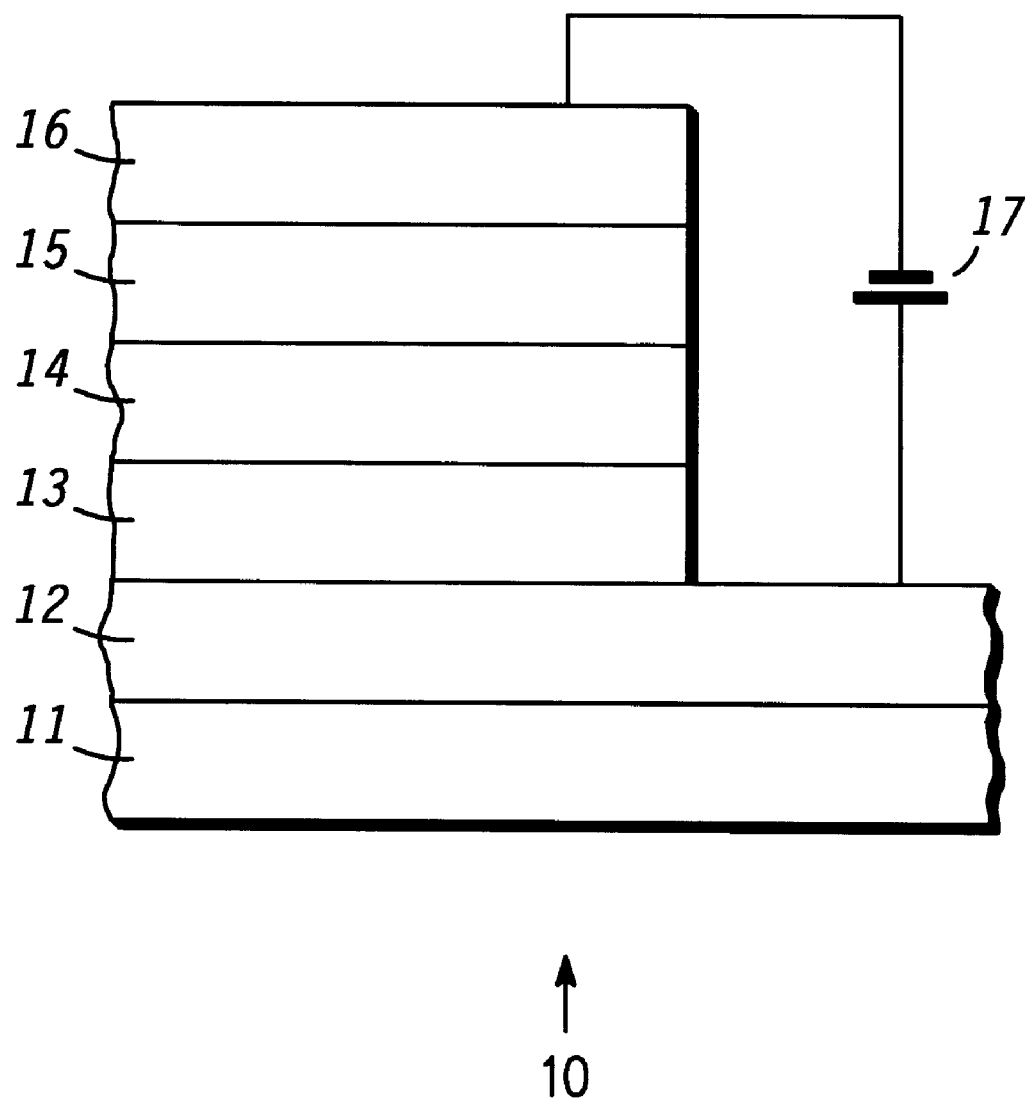
FIG. 1 is a simplified sectional view of a light emitting diode in accordance with the present invention.

FIG. 1 illustrates in a simplified cross-sectional view, one embodiment of an organic light emitting device (LED) 10.

Organic LED 10 includes a substrate 11 which in this specific embodiment is a glass plate having a relatively planar upper surface. An electrically conductive layer 12 is deposited on the planar surface of substrate 11 so as to form a relatively uniform electrical contact. A first organic layer 13 of hole transporting material is deposited on the surface of conductive layer 12. A second organic layer 14 of emissive material is deposited onto first organic layer 13. Then a third organic layer 15 of electron transporting material is deposited on the surface of layer 14 and a second electrically conductive layer 16 is deposited on the upper surface of third organic layer 15 to form a second electrical contact.

While it should be understood that light generated within second organic layer 14 can be emitted either through first organic layer 13, conductive layer 12 and substrate 11 or through third organic layer 15 and second conductive layer 16, in the present embodiment, substrate 11 is formed of glass and conductive layer 12 is formed of organic or inorganic conductors, such as conductive polyaniline (PANI), indium-tin-oxide (ITO), which are substantially transparent to visible light so that the emitted light exits downwardly through substrate 11 in the figure.

Further, in this embodiment, conductive layer 16 is formed of any of a wide range of metals or alloys in which at least one metal has a work function less than 4.0 ev. By the proper selection of material for conductive layer 16, the work functions of the materials making up layers 15 and 16 are substantially matched to reduce the required operating voltage and improve the efficiency of organic LED 10. Additional information on work function matching is disclosed in a copending U.S. Patent Application entitled "Organic LED with Improved Efficiency", filed on Sep. 12, 1994, application Ser. No. 08/304,454, and assigned to the same assignee.

Also, in FIG. 1 organic LED 10 has a potential applied between layers 12 and 16 by means of a potential source 17. In this embodiment conductive layer 12 is a p-type contact and conductive layer 16 is an n-type contact. The negative terminal of potential source 17 is connected to conductive layer 16 and the positive terminal is connected to conductive layer 12. Electrons injected from the n-type contact (layer 16) are transported through organic layer 15 and into organic layer 14 (the emissive layer). Holes injected from the p-type contact (layer 12) are transported through organic layer 13 and into organic layer 14 (the emissive layer), where upon an electron and a hole recombination a photon is emitted.

Organic layer 13 is made of any known hole transporting organic molecules, such as aromatic tertiary amines (U.S. Pat. No. 5,150,006) and/or hole transporting polymers such as poly(phenylene vinylene), and is used to transport holes into organic layer 14 and confine electrons in organic layer 14. Organic layer 15 is made of any known electron transporting materials, such as tris(8-hydroxyquinolino) aluminum (U.S. Pat. No. 4,539,507) and is used to transport electrons into organic layer 14 and confine holes within organic layer 14. Thus the holes and electrons have the maximum opportunity to recombine in organic layer 14 to give off light.

In general, it should be understood that organic layer 15 is optional, however, if organic LED 10 is modified by omitting organic layer 15, the device is still operational; but its operating efficiency is reduced. In some special applications it may be possible to eliminate organic layer 13 in addition to or instead of organic layer 15, however, it should again be understood that the efficiency and operating characteristics of organic LED 10 can be substantially modified.

In accordance with the present invention, organic layer 14 (the emissive layer) in organic LED 10 is formed of at least one organometallic complex having a general formula I or a general formula II as shown in the following:

Formula I

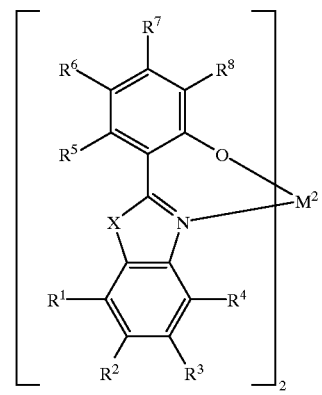

Formula II

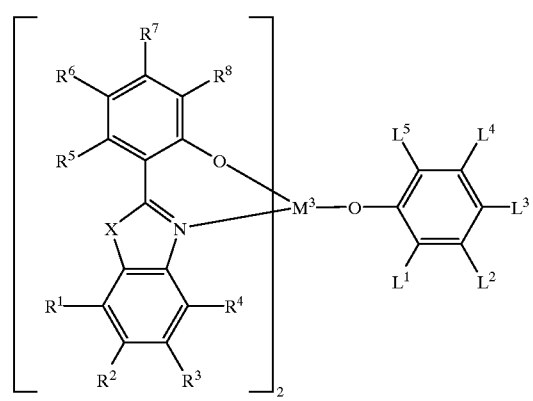

Where:

$M^2$ is a divalent metal, such as $Mg^{+2}$, $Zn^{+2}$, $Be^{+2}$ etc.;

$M^3$ is a trivalent metal, such as $Al^{+3}$, $Ga^{+3}$, $In^{+3}$ etc.;

X represents O, S, NH and $CH_2$ etc.;

R1 to R8 represent substitution possibilities at each position and each represent hydrogen or hydrocarbon groups or functional groups such as cyano, halogen, haloalkyl, haloalkoxy, alkoxyl, amido, amino, sulfonyl, carbonyl, carbonyloxy and oxycarbonyl etc.; and L1 to L5 represent substitution possibilities at each position and each represent hydrogen or hydrocarbon groups or functional groups such as cyano, halogen, haloalkyl, haloalkoxy, alkoxyl, amido, amino, sulfonyl, carbonyl, carbonyloxy and oxycarbonyl etc., with the provision that L1 and L2 together or L2 and L3 together can form a fused benzo ring.

The following are a few specific examples of preferred divalent organometallic complexes satisfying the requirements of the invention, where beryllium is used as an exemplary divalent metal:

Be-1
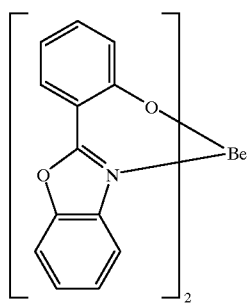
Be-2
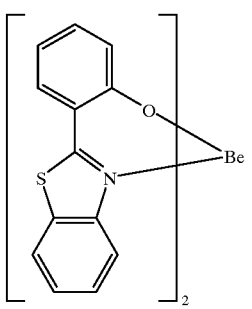
Be-3
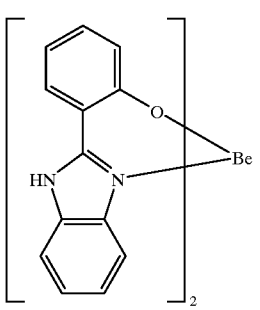
Be-4
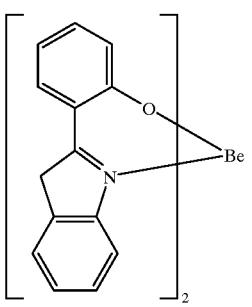
Be-5
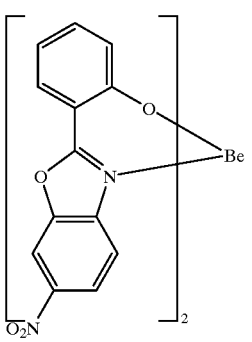
Be-6
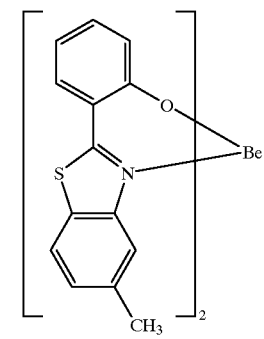
Be-7
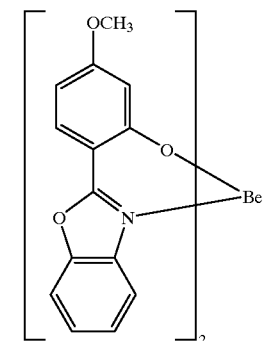
Be-8
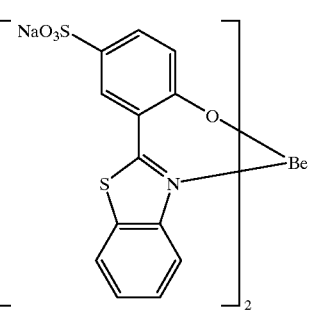
The following are a few specific examples of preferred trivalent organometallic complexes satisfying the requirements of the invention, where aluminum is used as an exemplary trivalent metal:
Al-1
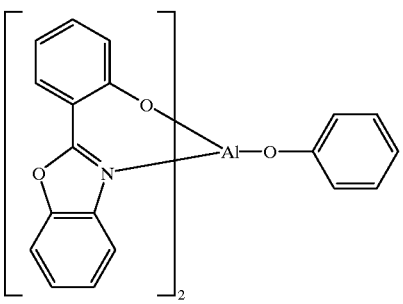

Al-2
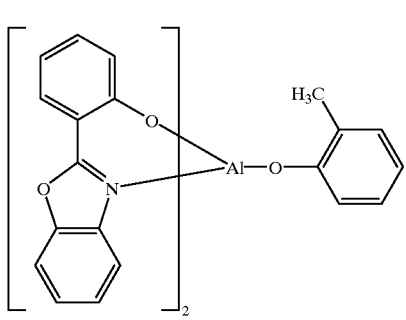

Al-3
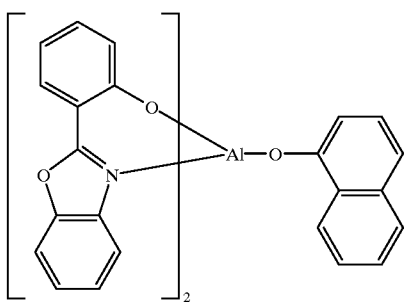

Al-4
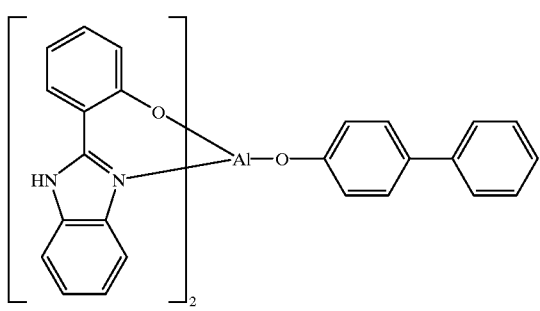

Al-5
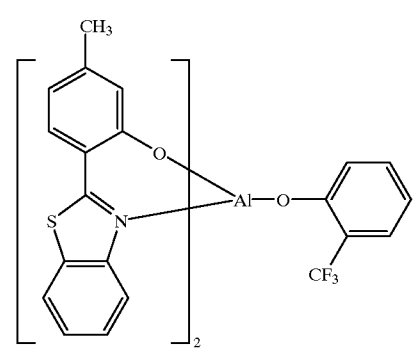

Al-6
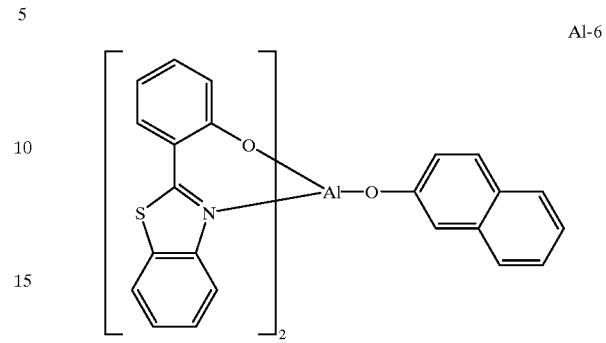

Organic layer 14 (the emissive layer) in organic LED 10, made of any of the above embodied organometallic complexes, is commonly deposited by thermal vapor deposition, electron beam evaporation, chemical deposition and the like. The emission peaks of typical 2-(2-hydroxyphenyl)benzoxazole-based organometallic complexes when utilized in organic LEDs range from 450 nm to 505 nm, which are in the regions of blue to bluish-green on the CIE 1931 chromaticity diagram. The emission peaks of typical 2-(2-hydroxyphenyl)benzothiazole-based organometallic complexes when utilized in organic LEDs range up to 546 nm, which are in the region of green on the CIE 1931 chromaticity diagram.

EXAMPLES

This invention will be further described by the following examples, which are intended to illustrate specific embodiments of the invention but not to limit its scope.

Example 1

The following procedure for synthesis of Be-1 (illustrated above) can be used to prepare all the divalent metal complexes disclosed in this invention, except that metal chloride salt, instead of metal sulfate salt, is used in some cases depending on the availability of the salts.

Be-1

A solution of 20 mmol of 2-(2-hydroxyphenyl) benzoxazole (Aldrich Chemical Company) in 80 mL of methanol is treated with 20 mmol of sodium hydroxide pellet (Fisher Scientific Company) under argon atmosphere. The mixture is stirred and heated at reflux until all the sodium hydroxide pellets are dissolved. After the reaction mixture has cooled down to room temperature, it is added with 10 mmol of beryllium sulfate tetrahydrate (Aldrich Chemical Company). The resulting mixture is stirred at reflux for 16 hours and allowed to cool to room temperature. The solid is collected by filtration and washed with methanol, and dried under vacuum to afford the title compound in 90% yield.

Example 2

The following procedure for synthesis of Al-1 (illustrated above) can be used to prepare all the trivalent metal complexes disclosed in this invention.

Al-1

A solution of 120 mmol of 2-(2-hydroxyphenyl) benzoxazole (Aldrich Chemical Company) and 60 mmol of phenol (Aldrich Chemical Company) in 300 mL of methanol is treated with 180 mmol of sodium hydroxide pellets (Fisher Scientific Company) under argon atmosphere. The mixture is stirred and heated at reflux until all the sodium hydroxide pellet are dissolved. After the reaction mixture has cooled down to room temperature, it is added with 60 mmol of aluminum chloride hexahydrate (Aldrich Chemical Company). The resulting mixture is stirred at reflux for 20 hours and allowed to cool to room temperature. The solid is collected by filtration and washed with methanol, and dried under vacuum to afford the title compound in 67% yield.

Example 3

The following procedure is used for the purification and characterization of the organometallic complexes disclosed in the invention.

A powder sample to be purified is placed into the sealed end of an one-end-sealed quartz tube which has been divided into several zones that are connected together with ground joints. The quartz tube is then inserted into a one-end-sealed Pyrex tube which has been connected to a vacuum system. The sealed end of the quartz tube is in contact with the sealed end of the Pyrex tube. The Pyrex tube is then evacuated to $10^{-6}$ torr with a diffusion pump and the sealed end of the Pyrex tube is heated in a tube furnace. The pure product is sublimed into different zones than volatile impurities in the quartz tube and purification thus is achieved. The sublimation temperature ranges from 250° C. to 350° C. depending on the complexes.

The pure complexes were analyzed and characterized by ultraviolet-visible, infrared, photoluminescence spectra as well as elemental analyses. This provided confirmation for the structures and compositions of the desired complexes.

Example 4

An organic EL device was fabricated in the following fashion:

(a) an indium tin oxide (ITO) coated glass substrate was ultrasonically cleaned in a commercial detergent, rinsed in deionized water, degreased in 2-propanol and acetone, and dried by blowing filtered nitrogen;

(b) a layer of polyaniline (PANI)(Uniax) having a thickness of 1000 Å was deposited over the ITO on the substrate by spin coating from a m-cresol solution;

(c) onto the PANI was deposited a 300 Å hole transporting layer of N,N'-dipheny-N,N'-(3-methylphenyl)-1,1'-biphenyl-4,4'-diamine (TPD) by vacuum evaporation from a tantalum boat;

(d) 300 Å of zinc 2-(2-oxo-phenyl)benzoxazole (ZnOPB) complex, as the emissive layer, was deposited onto the TPD layer, also by vacuum evaporation from a tantalum boat; and (e) over the emissive layer was deposited 10 Å of lithium, which was covered by 2000 Å of silver to complete the organic EL device. The lithium-silver combination served as the n-type contact.

In operation, bluish-green light became visible to the naked eye just above 9 volts forward bias. The emission color is near the boundary (on the CIE 1931 chromaticity diagram) between green and bluish-green. The device had a measured quantum efficiency (photons per electron) of 0.31% at 150 mA/cm$^2$ and a luminance of 2700 cd/m$^2$ at 15 volts forward bias.

Example 5

An organic EL device was constructed similarly as in example 4, except that between the emissive layer and the n-type contact, a 300 Å layer of tris(8-quinolinolate) aluminum was deposited by vacuum evaporation as an electron transporting layer.

Green light emission was visible to the naked eye when the device was forward biased just above 9 volts. The electroluminescence spectral peaks were shifted to over 500 nm, but a large shoulder of luminescence in the blue region remained. The device had a measured external quantum efficiency (photons per electron) of 0.62% at 85 mA/cm$^2$ and a luminance of 5400 cd/m$^2$ at 15 volts forward bias.

Example 6

An organic EL device was fabricated in the following fashion:

(a) an indium tin oxide (ITO) coated glass substrate was degreased in acetone and isopropyl alcohol. After drying by blowing filtered nitrogen, the substrate was further cleaned by standard UV-ozone processing;

(b) a layer of copper phthalocyanine (CuPc) having a thickness of 375 Å was deposited over the ITO on the substrate by thermal evaporation under vacuum;

(c) onto the top of the CuPc layer was deposited a 375 Å hole transporting layer of 4,4'-bis(N,N'-∂naphthylphenyl amino)-1,1'-biphenyl ("∂-NPB") by thermal evaporation under vacuum;

(d) 600 Å of zinc 2-(2-oxo-phenyl)benzoxazole complex, as the emissive layer, was deposited onto the ∂-NPB layer by thermal evaporation under vacuum;

(e) over the emissive layer was co-deposited 2000 Å of magnesium/silver in a 9.28:1 ratio as the cathode electrode for electron injection, which was then covered by 1000 Å of silver as a capping layer;

(f) the device was encapsulated, as disclosed in copending, commonly-assigned U.S. patent application Ser. No. 08/565,123, filed Nov. 30, 1995, now U.S. Pat. No. 5,811,177.

Figure 2:
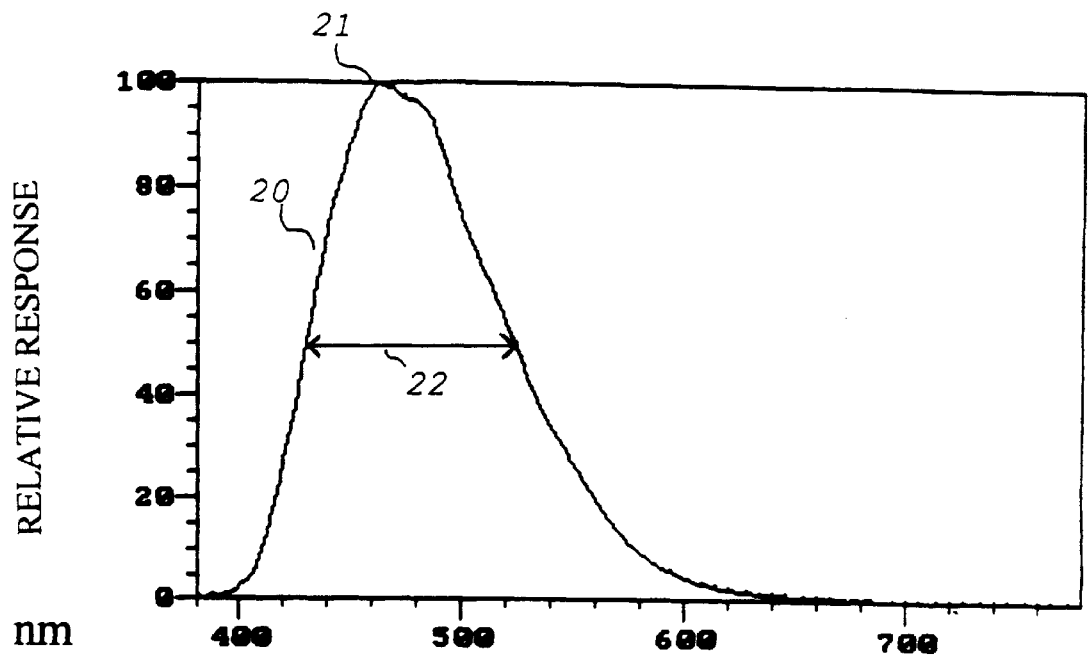
FIG. 2 is a spectral distribution curve of a first light emitting diode in accordance with the present invention.

In operation, the device emitted 123 cd/m$^2$ of blue light at 9.0 volts forward bias with current density of 20 mA/cm$^2$. The spectral distribution curve 20 of the light emitted from this device is shown in FIG. 2. The emission maximum 21 of the device is around 462 nm. The half band width 22 of the spectral distribution curve 20 is about 92 nm.

Example 7

An organic EL device was fabricated in the following fashion:

(a) an indium tin oxide (ITO) coated glass substrate was degreased in acetone and isopropyl alcohol. After drying by blowing filtered nitrogen, the substrate was further cleaned by standard UV-ozone processing;

(b) a layer of copper phthalocyanine (CuPc) having a thickness of 375 Å was deposited over the ITO on the substrate by thermal evaporation under vacuum;

(c) onto the top of the CuPc layer was deposited a 375 Å hole transporting layer of 4,4-bis(N,N'-∂naphthylphenyl amino)-1,1'-biphenyl ("∂-NPB") by thermal evaporation under vacuum;

(d) 600 Å of zinc 2-(2-oxo-phenyl)benzothiazole complex, as the emissive layer, was deposited onto the ∂-NPB layer by thermal evaporation under vacuum;

(e) over the emissive layer was co-deposited 2000 Å of magnesium/silver in a 9.00:1 ratio as the cathode electrode for electron injection.

Figure 3:
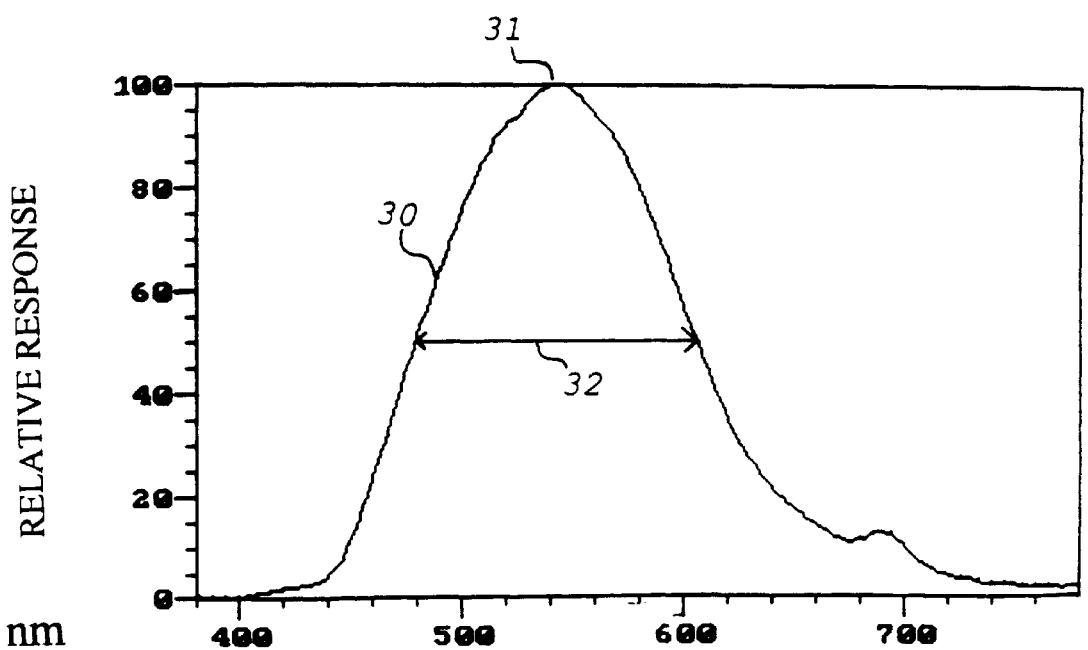
FIG. 3 is a spectral distribution curve of a second light emitting diode in accordance with the present invention.

In operation, the device emits 188 cd/m² of green light at 7.4 volts forward bias with current density of 20 mA/cm². The spectral distribution curve 30 of the light emitted from this device is shown in FIG. 3. The emission maximum 31 of the device is around 540 nm. The half band width 32 of the spectral distribution curve 30 is about 129 nm.

Thus it is seen that benzothiazole-based EL devices perform unexpectedly differently from benzoxazole-based EL devices. One would have expected substantially similar spectra from benzothiazole- and benzoxazole-based EL devices. However: (a) benzothiazole-based EL devices emit over a broader range of the visible spectrum, thereby making them better suited for displaying in multiple colors (as seen in FIGS. 2 and 3, the half band width 32 of the benzothiazole-based EL device of Example 7 is about 129 nm compared to the half band width 22 of the benzoxazole-based EL device of Example 6 which is only about 92 nm); (b) benzothiazole-based EL devices emit substantial quantities of blue, green, yellow and orange light compared to the green, yellow and orange light emitted by benzoxazole-based EL devices (compare the spectral distribution curve 30 of the benzothiazole-based device of Example 7 in FIG. 3 to the spectral distribution curve 20 of the benzoxazole-based device of Example 6 in FIG. 2); (c) the human eye perceives the light emitted by benzothiazole-based EL devices to be green, instead of blue as with benzoxazole-based devices; and (d) benzothiazole-based EL devices require lower driving voltages than benzoxazole-based devices (compare 7.4 V for the benzothiazole-based device of Example 7 to 9.0 V for the benzoxazole-based device of Example 6).

Thus, a class of new organometallic complexes for use in light emitting devices has been disclosed, along with preparation methods for the disclosed organometallic complexes and methods of fabrication of light emitting devices. The new organometallic complexes have substantially improved efficiency and luminance, and especially in the blue range. The efficiency and luminance can be further improved by 2–5 times by dye doping as disclosed in the prior art.

While I have shown and described specific embodiments of the present invention, further modifications and improvements will occur to those skilled in the art. I desire it to be understood, therefore, that this invention is not limited to the particular forms shown and I intend in the appended claims to cover all modifications that do not depart from the spirit and scope of this invention.

What is claimed is:

1. An organic light emitting device comprising:

a first conductive layer having a first conductivity;

a layer of first carrier transporting and second carrier blocking material positioned on the first conductive layer;

a layer of organometallic emissive material positioned on the layer of first carrier transporting and second carrier blocking material, the organometallic emissive material having one of the general formulas

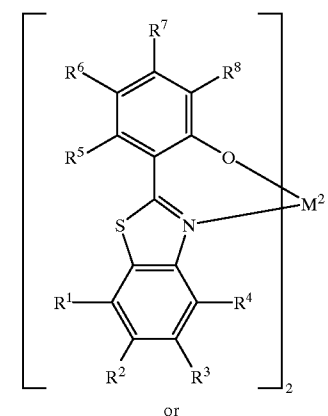

or

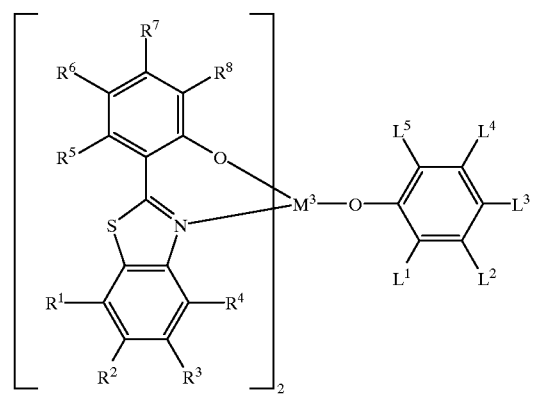

where:

$M^2$ is a divalent metal, $M^3$ is a trivalent metal,

R1 to R8 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl, and L1 to L5 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl;

a layer of second carrier transporting and first carrier blocking material positioned on the layer of organometallic emissive material; and a second conductive layer having a second conductivity positioned on the layer of second carrier transporting and first carrier blocking material.

2. An organic light emitting device as claimed in claim 1 wherein $M^2$ is a divalent metal selected from the following group: $Mg^{+2}$, $Zn^{+2}$, and $Be^{+2}$.

3. An organic light emitting device as claimed in claim 1 wherein $M^3$ is a trivalent metal selected from the following group: $Al^{+3}$, $Ga^{+3}$, and $In^{+3}$.

4. An organic light emitting device as claimed in claim 1 with the additional provision that L1 and L2 together or L2 and L3 together form a fused benzo ring.

5. An organic light emitting device as claimed in claim 1 wherein the first carriers are holes and the second carriers are electrons.

6. An organic light emitting device as claimed in claim 5 wherein the first conductive layer has p-conductivity and the second conductive layer has n-conductivity.

7. An organic light emitting device as claimed in claim 1 wherein one of the first or second conductive layers is transparent to light emitted by the layer of organometallic emissive material.

8. An organic light emitting device as claimed in claim 1 wherein the layer of organometallic emissive material has one of the following formulas:

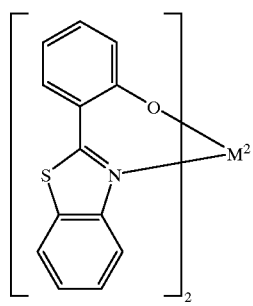

M²-4

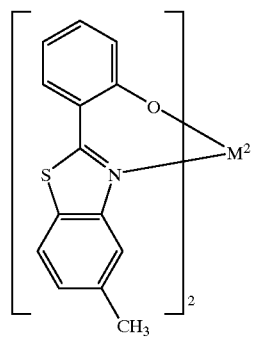

M²-5

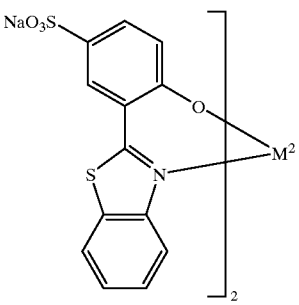

M²-6 where M² is a divalent metal.

9. An organic light emitting device as claimed in claim 1 wherein the organometallic emissive material has one of the following formulas:

M³-4

M³-5 where M³ is a trivalent metal.

10. A method of fabricating an organic light emitting diode comprising the steps of:

providing a glass substrate having a substantially planar surface;

depositing a transparent electrically conductive layer on the planar surface of the glass substrate;

depositing a hole transporting layer of organic material on the transparent electrically conductive layer;

depositing an emissive layer of organic material on the hole transporting layer, the emissive layer including organometallic material having one of the general formulas

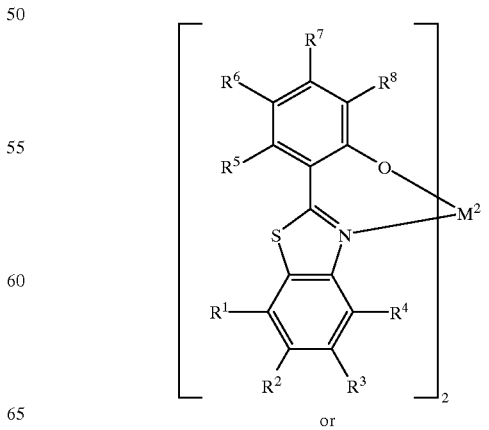

or

-continued

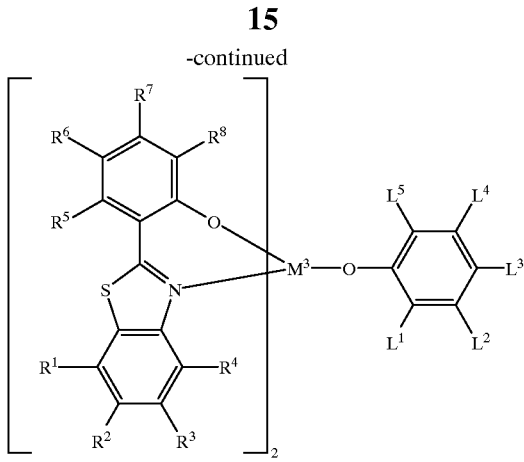

where:
- $M^2$ is a divalent metal,
- $M^3$ is a trivalent metal,
- R1 to R8 represent substitution possibilities at each position and each represent hydrogen or hydrocarbon groups or functional groups, wherein functional groups represented by R1 to R8 are selected from the following group: cyano, halogen, haloalkyl, haloalkoxy, alkoxyl, amido, amino, sulfonyl, carbonyl, carbonyloxy and oxycarbonyl,
- L1 to L5 represent substitution possibilities at each position and each represent hydrogen or hydrocarbon groups or functional groups, wherein functional groups represented by L1 to L5 are selected from the following group: cyano, halogen, haloalkyl, haloalkoxy, alkoxyl, amido, amino, sulfonyl, carbonyl, carbonyloxy and oxycarbonyl; and depositing an electrically conductive contact on the emissive layer.

11. An organic light emitting device comprising:
  a first conductive layer having a first conductivity;
  a layer of first carrier transporting and second carrier blocking material positioned on the first conductive layer;
  a layer of organometallic emissive material positioned on the layer of first carrier transporting and second carrier blocking material, the organometallic emissive material having one of the general formulas

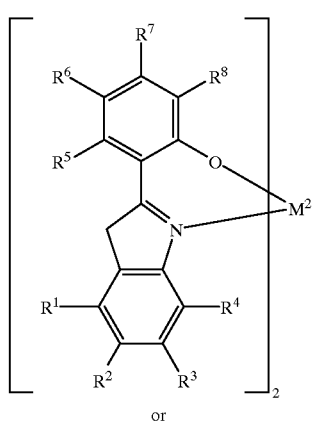

or

-continued

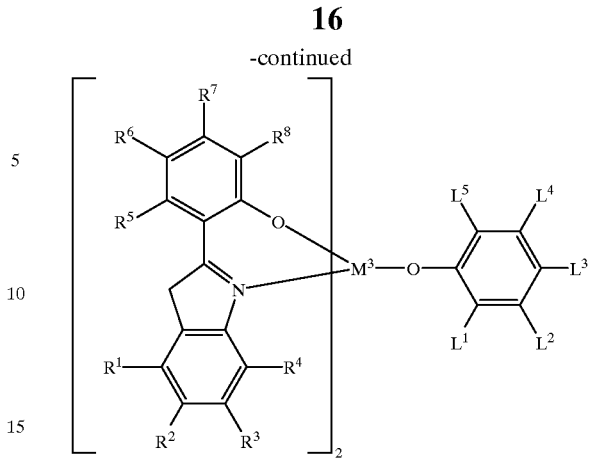

where:
- $M^2$ is a divalent metal,
- $M^3$ is a trivalent metal,
- R1 to R8 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl, and
- L1 to L5 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl;

a layer of second carrier transporting and first carrier blocking material positioned on the layer of organometallic emissive material; and a second conductive layer having a second conductivity positioned on the layer of second carrier transporting and first carrier blocking material.

12. An organic light emitting device as claimed in claim 11 wherein $M^2$ is a divalent metal selected from the following group: $Mg^{+2}$, $Zn^{+2}$, and $Be^{+2}$.

13. An organic light emitting device as claimed in claim 11 wherein $M^3$ is a trivalent metal selected from the following group: $Al^{+3}$, $Ga^{+3}$, and $In^{+3}$.

14. An organic light emitting device as claimed in claim 11 with the additional provision that L1 and L2 together or L2 and L3 together form a fused benzo ring.

15. An organic light emitting device as claimed in claim 11 wherein the first carriers are holes and the second carriers are electrons.

16. An organic light emitting device as claimed in claim 15 wherein the first conductive layer has p-conductivity and the second conductive layer has n-conductivity.

17. An organic light emitting device as claimed in claim 11 wherein one of the first or second conductive layers is transparent to light emitted by the layer of organometallic emissive material.

18. An organic light emitting device as claimed in claim 11 wherein the layer of organometallic emissive material has the following formula:

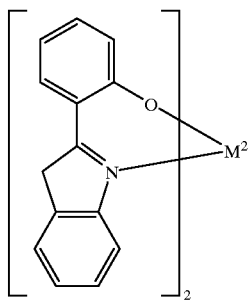

where M² is a divalent metal.

19. A method of fabricating an organic light emitting diode comprising the steps of:
  providing a glass substrate having a substantially planar surface;
  depositing a transparent electrically conductive layer on the planar surface of the glass substrate;
  depositing a hole transporting layer of organic material on the transparent electrically conductive layer;
  depositing an emissive layer of organic material on the hole transporting layer, the emissive layer including organometallic material having one of the general formulas

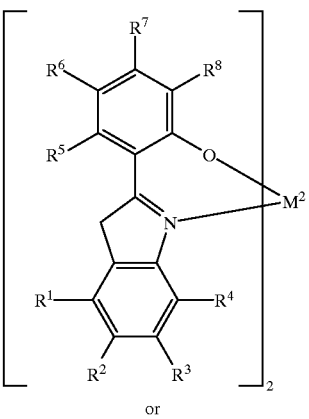

or

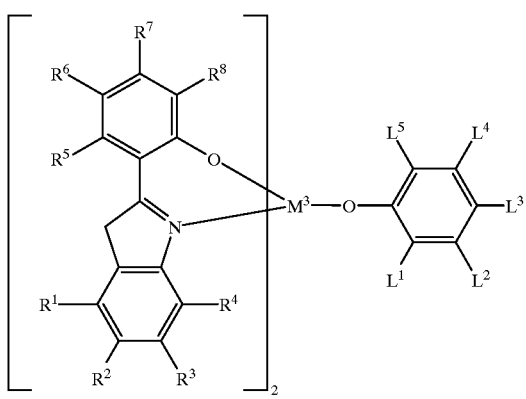

where:
  M² is a divalent metal,
  M³ is a trivalent metal,
  R1 to R8 represent substitution possibilities at each position and each represent hydrogen or hydrocarbon groups or functional groups, wherein functional groups represented by R1 to R8 are selected from the following group: cyano, halogen, haloalkyl, haloalkoxy, alkoxyl, amido, amino, sulfonyl, carbonyl, carbonyloxy and oxycarbonyl, and
  L1 to L5 represent substitution possibilities at each position and each represent hydrogen or hydrocarbon groups or functional groups, wherein functional groups represented by L1 to L5 are selected from the following group: cyano, halogen, haloalkyl, haloalkoxy, alkoxyl, amido, amino, sulfonyl, carbonyl, carbonyloxy and oxycarbonyl; and
depositing an electrically conductive contact on the emissive layer.

20. An organic light emitting device comprising:
  a first conductive layer having a first conductivity;
  a layer of first carrier transporting and second carrier blocking material positioned on the first conductive layer;
  a layer of organometallic emissive material positioned on the layer of first carrier transporting and second carrier blocking material, the organometallic emissive material having one of the general formulas

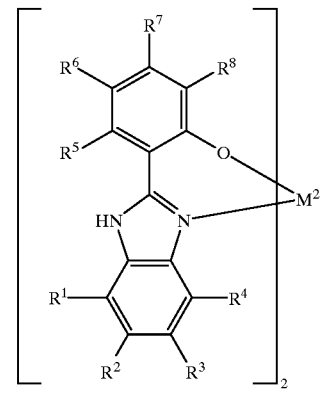

or

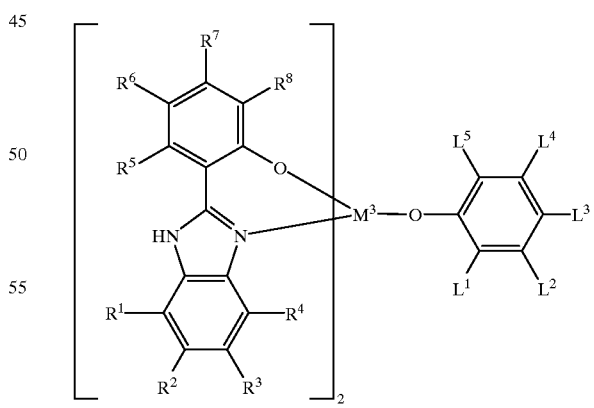

where:
  M² is a divalent metal,
  M³ is a trivalent metal,
  R1 to R8 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl, and L1 to L5 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl;

a layer of second carrier transporting and first carrier blocking material positioned on the layer of organometallic emissive material; and a second conductive layer having a second conductivity positioned on the layer of second carrier transporting and first carrier blocking material.

21. An organic light emitting device as claimed in claim 20 wherein $M^2$ is a divalent metal selected from the following group: $Mg^{+2}$, $Zn^{+2}$, and $Be^{+2}$.

22. An organic light emitting device as claimed in claim 20 wherein $M^3$ is a trivalent metal selected from the following group: $Al^{+3}$, $Ga^{+3}$, and $In^{+3}$.

23. An organic light emitting device as claimed in claim 20 with the additional provision that L1 and L2 together or L2 and L3 together form a fused benzo ring.

24. An organic light emitting device as claimed in claim 20 wherein the first carriers are holes and the second carriers are electrons.

25. An organic light emitting device as claimed in claim 24 wherein the first conductive layer has p-conductivity and the second conductive layer has n-conductivity.

26. An organic light emitting device as claimed in claim 20 wherein one of the first or second conductive layers is transparent to light emitted by the layer of organometallic emissive material.

27. An organic light emitting device as claimed in claim 20 wherein the layer of organometallic emissive material has the following formula:

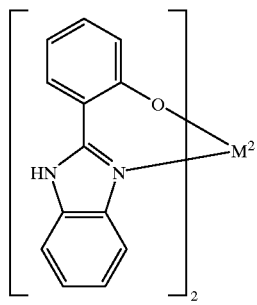

$M^2$-8 where $M^2$ is a divalent metal.

28. An organic light emitting device as claimed in claim 20 wherein the organometallic emissive material has the following formula:

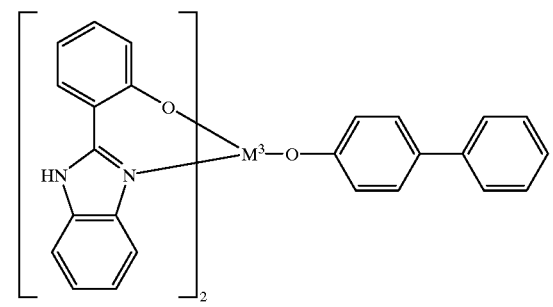

$M^3$-6 where $M^3$ is a trivalent metal.

29. A method of fabricating an organic light emitting diode comprising the steps of:

providing a glass substrate having a substantially planar surface;

depositing a transparent electrically conductive layer on the planar surface of the glass substrate;

depositing a hole transporting layer of organic material on the transparent electrically conductive layer;

depositing an emissive layer of organic material on the hole transporting layer, the emissive layer including organometallic material having one of the general formulas

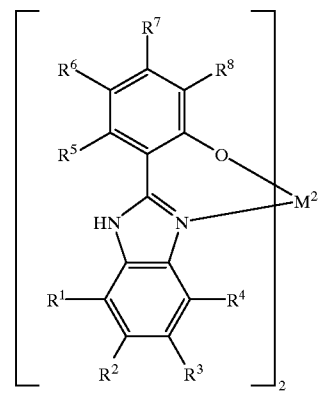

or

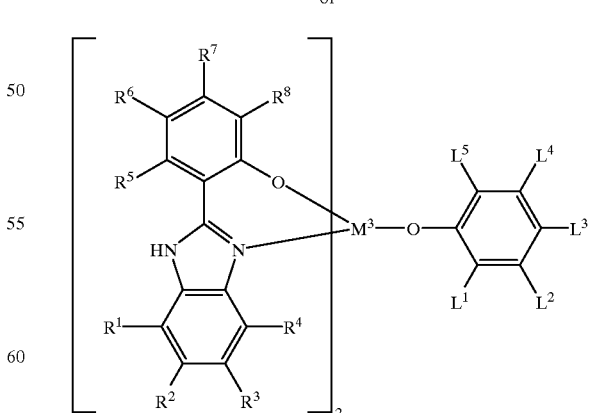

where:

$M^2$ is a divalent metal, $M^3$ is a trivalent metal,

R1 to R8 represent substitution possibilities at each position and each represent hydrogen or hydrocarbon groups or functional groups, wherein functional groups represented by R1 to R8 are selected from the following group: cyano, halogen, haloalkyl, haloalkoxy, alkoxyl, amido, amino, sulfonyl, carbonyl, carbonyloxy and oxycarbonyl, L1 to L5 represent substitution possibilities at each position and each represent hydrogen or hydrocarbon groups or functional groups, wherein functional groups represented by L1 to L5 are selected from the following group: cyano, halogen, haloalkyl, haloalkoxy, alkoxyl, amido, amino, sulfonyl, carbonyl, carbonyloxy and oxycarbonyl; and depositing an electrically conductive contact on the emissive layer.

30. An organic light emitting device comprising:

first and second conductive layers having organometallic material positioned therebetween, the organometallic material having one of the general formulas

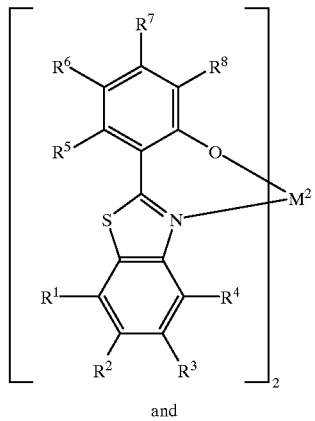

and

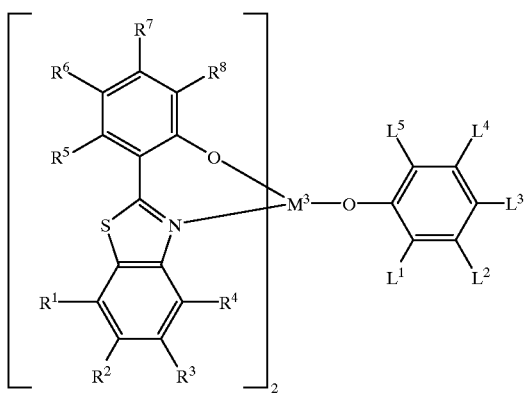

where:

M² is a divalent metal;

M³ is a trivalent metal;

R1 to R8 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl; and L1 to L5 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl.

31. An organic light emitting device comprising:

first and second conductive layers having organometallic material positioned therebetween, the organometallic material having one of the general formulas

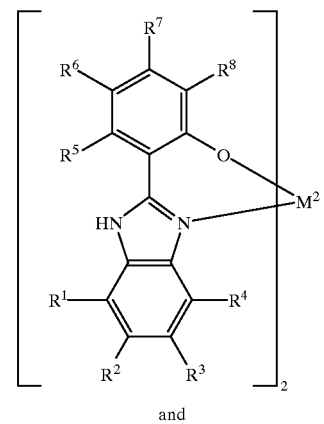

and

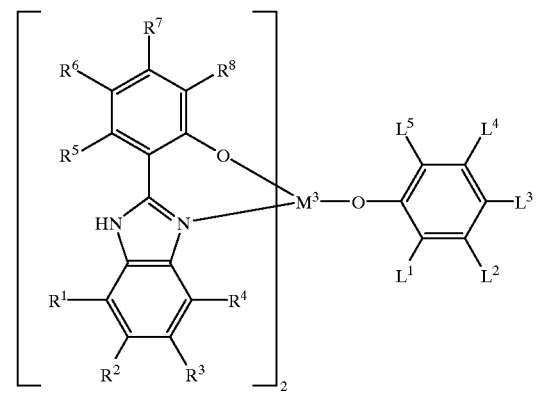

where:

M² is a divalent metal;

M³ is a trivalent metal;

R1 to R8 represent substitution possibilities at each position and each represent hydrogen or hydrocarbon groups or functional group selected from the following group: cyano, halogen, haloalkyl, haloalkoxy, alkoxyl, amido, amino, sulfonyl, carbonyl, carbonyloxy and oxycarbonyl; and L1 to L5 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl.

32. An organic light emitting device comprising:

first and second conductive layers having organometallic material positioned therebetween, the organometallic material having one of the general formulas

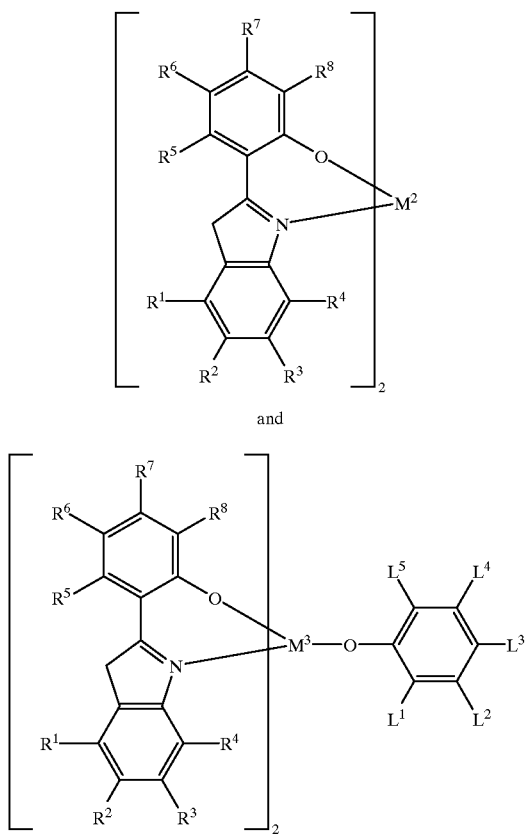

and

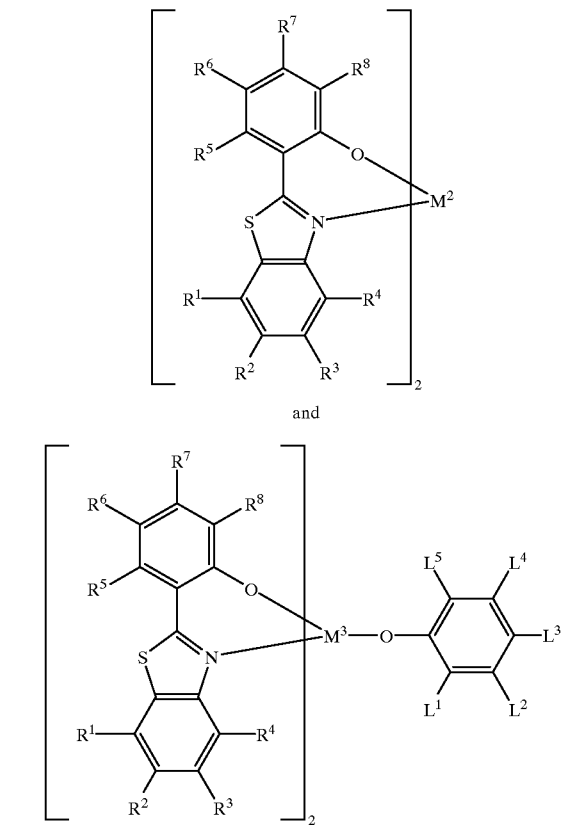

and where:

M² is a divalent metal;

M³ is a trivalent metal;

R1 to R8 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl; and L1 to L5 represent substitution possibilities at each position and each represent hydrogen or hydrocarbon groups or functional groups selected from the following group: cyano, halogen, haloalkyl, haloalkoxy, alkoxyl, amido, amino, sulfonyl, carbonyl, carbonyloxy and oxycarbonyl.

33. A method of fabricating an organic light emitting diode comprising the steps of:

providing a glass substrate having a substantially planar surface;

depositing a transparent electrically conductive layer on the planar surface of the glass substrate;

depositing organic material on the electrically conductive layer, the organic material including organometallic material having one of the general formulas where:

M² is a divalent metal;

M³ is a trivalent metal;

R1 to R8 represent substitution possibilities at each position and each represent hydrogen or hydrocarbon groups or functional groups, wherein functional groups represented by R1 to R8 are selected from the following group: cyano, halogen, haloalkyl, haloalkoxy, alkoxyl, amido, amino, sulfonyl, carbonyl, carbonyloxy and oxycarbonyl;

L1 to L5 represent substitution possibilities at each position and each represent hydrogen or hydrocarbon groups or functional groups, wherein functional groups represented by L1 to L5 are selected from the following group: cyano, halogen, haloalkyl, haloalkoxy, alkoxyl, amido, amino, sulfonyl, carbonyl, carbonyloxy and oxycarbonyl; and depositing an electrically conductive contact on the organic material.

34. A method of fabricating an organic light emitting diode comprising the steps of:

providing a glass substrate having a substantially planar surface;

depositing a transparent electrically conductive layer on the planar surface of the glass substrate;

depositing organic material on the electrically conductive layer, the organic material including organometallic material having one of the general formulas

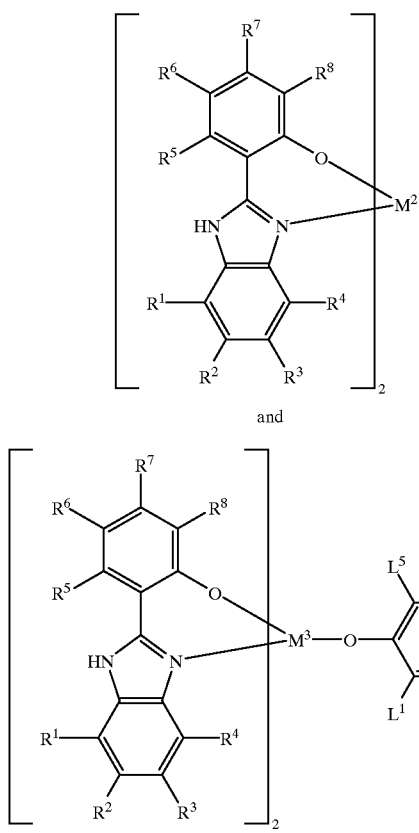

and where:

M² is a divalent metal;

M³ is a trivalent metal;

R1 to R8 represent substitution possibilities at each position and each represent hydrogen or hydrocarbon groups or functional groups, wherein functional groups represented by R1 to R8 are selected from the following group: cyano, halogen, haloalkyl, haloalkoxy, alkoxyl, amido, amino, sulfonyl, carbonyl, carbonyloxy and oxycarbonyl;

L1 to L5 represent substitution possibilities at each position and each represent hydrogen or hydrocarbon groups or functional groups, wherein functional groups represented by L1 to L5 are selected from the following group: cyano, halogen, haloalkyl, haloalkoxy, alkoxyl, amido, amino, sulfonyl, carbonyl, carbonyloxy and oxycarbonyl; and depositing an electrically conductive contact on the organic material.

35. A method of fabricating an organic light emitting diode comprising the steps of:

providing a glass substrate having a substantially planar surface;

depositing a transparent electrically conductive layer on the planar surface of the glass substrate;

depositing organic material on the electrically conductive layer, the organic material including organometallic material having one of the general formulas

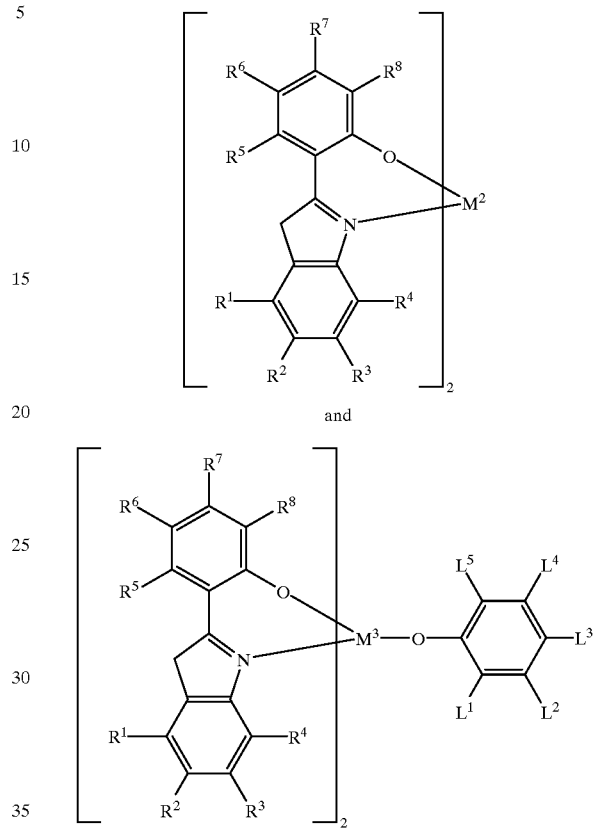

and where:

M² is a divalent metal;

M³ is a trivalent metal;

R1 to R8 represent substitution possibilities at each position and each represent hydrogen or hydrocarbon groups or functional groups, wherein functional groups represented by R1 to R8 are selected from the following group: cyano, halogen, haloalkyl, haloalkoxy, alkoxyl, amido, amino, sulfonyl, carbonyl, carbonyloxy and oxycarbonyl;

L1 to L5 represent substitution possibilities at each position and each represent hydrogen or hydrocarbon groups or functional groups, wherein functional groups represented by L1 to L5 are selected from the following group: cyano, halogen, haloalkyl, haloalkoxy, alkoxyl, amido, amino, sulfonyl, carbonyl, carbonyloxy and oxycarbonyl; and depositing an electrically conductive contact on the organic material.

* * * * *